(12) United States Patent
Jezek et al.

(10) Patent No.: US 9,278,157 B2
(45) Date of Patent: Mar. 8, 2016

(54) NITRIC OXIDE-GENERATING SKIN DRESSINGS

(71) Applicant: Insense Limited, Bedford (GB)

(72) Inventors: Jan Jezek, Stanwick (GB); Lynne Patricia Watson, Wootton (GB)

(73) Assignee: Insense Limited, Bedford (GB)

( * ) Notice: Subject to any disclaimer, the term of this patent is extended or adjusted under 35 U.S.C. 154(b) by 0 days.

(21) Appl. No.: 14/511,555

(22) Filed: Oct. 10, 2014

(65) Prior Publication Data
US 2015/0030702 A1   Jan. 29, 2015

Related U.S. Application Data

(63) Continuation-in-part of application No. 12/671,965, filed as application No. PCT/GB2008/050564 on Jul. 14, 2008, now abandoned.

(30) Foreign Application Priority Data

Aug. 9, 2007  (GB) .................................. 0715556.7

(51) Int. Cl.
*A61L 15/08*  (2006.01)
*A61L 15/14*  (2006.01)
*A61L 26/00*  (2006.01)

(52) U.S. Cl.
CPC ........... *A61L 26/0004* (2013.01); *A61L 26/008* (2013.01); *A61L 26/0061* (2013.01); *A61L 26/0066* (2013.01); *A61L 2300/114* (2013.01)

(58) Field of Classification Search
None
See application file for complete search history.

(56) References Cited

U.S. PATENT DOCUMENTS

| 5,648,101 A | 7/1997 | Tawashi |
| 6,103,275 A | 8/2000 | Seitz et al. |
| 6,709,681 B2 | 3/2004 | Benjamin et al. |
| 2003/0012816 A1 | 1/2003 | West et al. |
| 2003/0045865 A1 | 3/2003 | Knapp |

FOREIGN PATENT DOCUMENTS

| WO | WO 00/53193 | 9/2000 |
| WO | WO 01/96422 | 12/2001 |
| WO | WO 02/20026 | 3/2002 |
| WO | WO 03/090800 | 11/2003 |
| WO | WO 2006/095193 | 9/2006 |

OTHER PUBLICATIONS

International Search Report for corresponding International Application No. PCT/GB2008/050564, dated Oct. 21, 2009.
UK Intellectual Property Office Search Report for GB0715556.7, dated Dec. 6, 2007.

*Primary Examiner* — Kevin S Orwig
(74) *Attorney, Agent, or Firm* — DASCENZO Intellectual Property Law, P.C.

(57) ABSTRACT

A skin dressing is provided comprising a first component including a source of protons, a second component including a nitrite salt, the skin dressing further comprising a non-thiol reductant. The skin dressing is adapted, such that, when the first and second components are brought together and applied to a skin site the nitrite reacts to generate nitric oxide, increasing the pH of the dressing in contact with the skin site from an acidic value to a more neutral value.

15 Claims, 1 Drawing Sheet

NITRIC OXIDE-GENERATING SKIN DRESSINGS

RELATED APPLICATIONS

This application is a continuation-in-part and claims priority under 35 U.S.C. §120 to U.S. patent application Ser. No. 12/671,965, which was filed on Feb. 3, 2010, and which claims priority from PCT Patent Application No. PCT/GB2008/050564, which was filed on Jul. 14, 2008. PCT Patent Application No. PCT/GB2008/050564 claims priority from United Kingdom Patent Application No. 0715556.7, which was filed on Aug. 9, 2007. The complete disclosures of the above-identified patent applications are hereby incorporated by reference.

FIELD

The present disclosure relates to skin dressings for application to a part of a human or animal body for treatment of skin (for therapeutic or cosmetic purposes).

BACKGROUND

Under normal conditions, nitric oxide (NO) is a short-lived, unstable gaseous substance. Its instability is due to the unpaired electron of nitrogen. As an unstable substance with an unpaired electron, nitric oxide can be described as a free radical. However, compared with typical free radicals (e.g. hydroxyl radical or superoxide), whose life-time is in the order of milliseconds, nitric oxide is relatively stable. Typically, it is converted to a more stable chemical species within seconds of its production. Thus, for example, if gaseous nitric oxide contacts air, it reacts rapidly with oxygen to generate nitrogen dioxide as follows:

$$2NO+O_2 \rightarrow 2NO_2 \rightarrow N_2O_4$$

Under some conditions, for instance in pure gaseous state, NO can be stored without significant losses for a very long time. NO is a very hydrophobic compound and its solubility in water is therefore limited. Maximum solubility in water achievable under normal conditions is approximately 1.7 mM, the solubility being similar to that of oxygen. The oxidation of dissolved nitric oxide by dissolved oxygen occurs in aqueous solutions. Nevertheless, given the rate constants and low concentrations of dissolved NO and $O_2$ this reaction is considerably less rapid than in the gaseous state, where the concentration of oxygen is very high.

Nitric oxide can be produced by chemical reduction of nitrous acid. Many different reducing agents can be used to reduce nitrous acid, physiologically acceptable examples of such reducing agents include iodide anion, ascorbic acid, butylated hydroquinone, tocopherol etc. Nitrous acid is a weak acid with $pK_a$ 3.4. This means that at pH 3.4, nitrous acid exists as an equimolar mixture of nitrous acid ($HNO_2$) and nitrite ($NO_2^-$). At higher pH, the equilibrium shifts in favour of nitrite anion; at lower pH the equilibrium shifts in favour of nitrous acid. Since only nitrous acid can be chemically reduced to nitric oxide the efficiency of converting nitrite into nitric oxide increases with decreasing pH. So, whilst at pH 6 the rate of such conversion is negligible, it proceeds slowly at pH 5 and is very rapid at pH<4 and especially at pH<3.

A special category of reducing agents that react with nitrite in an acidic environment are thiols. Reaction between thiols and nitrite in an acidic environment does not result in nitrous acid reduction and immediate generation of nitric oxide, as in the case of other reducing agents. Instead, thiols are nitrosylated by nitrosonium cation ($NO^+$) which is another species generated from nitrite in acidic conditions.

Nitric oxide has a multitude of effects in living tissues. The mechanism of these effects is nearly always based on interaction of nitric oxide either with a metal component (typically iron) or with thiol groups of key enzymes and other proteins. Depending on the particular enzyme, such interaction can lead to either activation or inhibition of the protein. An example of an effect based on the activation of an enzyme is that of vasodilatation: nitric oxide binds to the haem iron of the enzyme guanylate cyclase, which results in conformational change exposing the catalytic site of the enzyme. This leads to catalytic conversion of GTP to cGMP. This conversion initiates the whole cascade of reactions leading to protein phosphorylation and muscle relaxation (vasodilatation). Other effects based on activation of enzymes or growth factors by nitric oxide include stimulation of cell division (proliferation) and cell maturation, stimulation of cell differentiation and formation of cell receptors, neovascularisation, formation of fibroblasts in the wound and thereby enhancement of collagen formation, etc.

Topical delivery of nitric oxide can be a very useful feature in various therapeutic or cosmetic applications including wound healing, treatment of skin or nail infections, sexual dysfunction etc.

U.S. Pat. No. 6,103,275 discloses a method for therapeutically applying nitric oxide, the method comprising bringing together a nitrite salt, a reductant and an acid with $pK_a$ between about 1 and about 4 at a body site.

The pH range at which the method should be used is not specified. However, the fact that the buffer components are referred to as acids may indicate that these compounds are predominantly present in the protonated form, therefore the pH of the composition should be substantially lower than 4. The presence of acids with pKa less than 4 (e.g. between 1 to 4) ensures good buffering capacity of the formulation at the required pH. Whilst incorporation of such acids is a convenient way of ensuring that pH is maintained at a level such that a continuous efficiency of converting nitrite to nitric oxide is maintained, there are disadvantages of introducing these acids into the system. Prolonged exposure of skin to any topical application that is buffered strongly at pH less than 4 is potentially harmful and should be avoided.

Other nitric oxide releasing systems have been disclosed. For example, U.S. Pat. No. 6,709,681 discloses a method of treating microbial infection, the method comprising mixing acidifying agent with a source of nitrite. In principle, this method is very similar to that disclosed in U.S. Pat. No. 6,103,275, i.e. mixing a source of nitrite with acids of $pK_a$ between 1 to 4. Importantly, the absence of strong reducing agents in the formulation disclosed in U.S. Pat. No. 6,709,681 does not ensure sufficient reducing power in the formulation. Consequently, generation of nitric oxide will be accompanied by direct generation of nitrogen dioxide according to the following mechanism:

$$NO_2^- + H^+ \rightarrow HNO_2$$

$$2HNO_2 \rightarrow NO + NO_2 + H_2O$$

Whilst nitric dioxide may exert good antimicrobial properties, it does not have vasodilating properties nor is it capable of activation of the cell proliferation. It is therefore generally desirable to stop the direct generation of nitrogen dioxide by incorporating the reducing agent.

U.S. 2003012816 discloses a biocompatible polymerisable macromer composition comprising a macromer having at least one nitric oxide carrying region or nitric oxide modulating compound wherein the nitric oxide or the nitric oxide modulating compound is released from the macromer and wherein the macromer further comprises one or more regions selected from the group consisting of a water soluble region, a cell adhesion ligand and a polymerisable region. The disclosed macromers include acrylolyl-PEG-Cys-NO macromer, acrylolyl-PEG-Lys5-NO macromer, PEG-DETA-NO macromer, PVA-NH2-NO macromer, PVA-Cys-NO macromer and PVA-NO-bFGF macromer.

SUMMARY

A skin dressing is provided comprising a first component including a source of protons, a second component including a nitrite salt, the skin dressing further comprising a non-thiol reductant. The skin dressing is adapted, such that, when the first and second components are brought together and applied to a skin site the nitrite reacts to generate nitric oxide, increasing the pH of the dressing in contact with the skin site from an acidic value to a more neutral value.

DESCRIPTION

Figure 1:
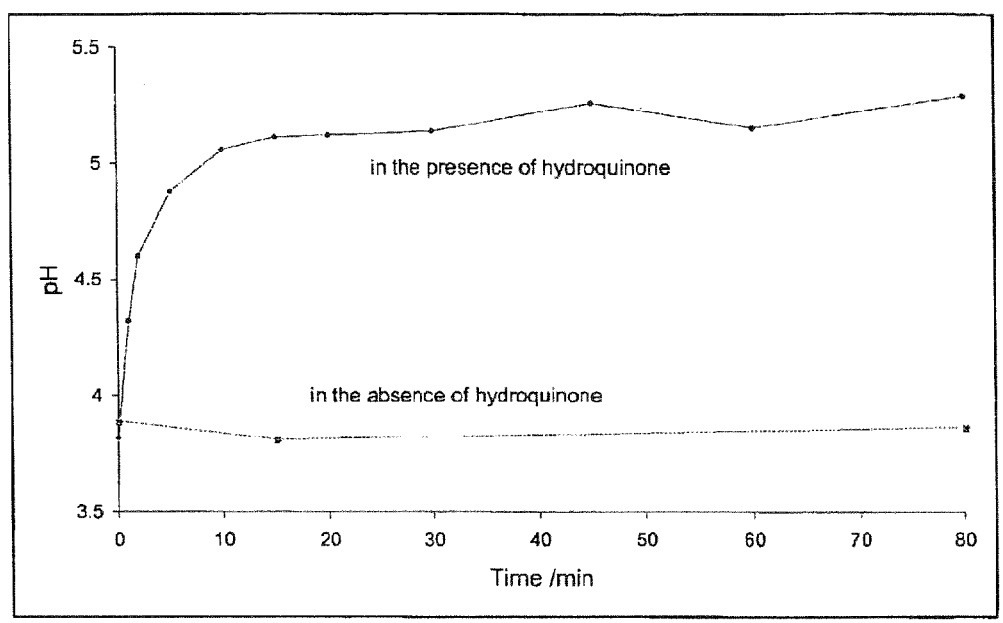
FIG. 1 is a graph of pH versus time (in minutes) showing the effect of hydroquinone (30 mM) on the pH of acidified nitrite (30 mM). Nitrite was acidified by addition of hydrochloric acid (final concentration 10 mM). The pH was measured prior to addition of hydroquinone and then at time-points indicated following addition of hydroquinone.

The present disclosure relates to skin dressings for application to a part of a human or animal body for treatment of skin (for therapeutic or cosmetic purposes), and relates particularly (but not exclusively) to wound dressings for treatment of compromised skin, particularly skin lesions, i.e. any interruption in the surface of the skin, whether caused by injury or disease, including skin ulcers, burns, cuts, punctures, lacerations, blunt traumas, acne lesions, boils etc. The term "skin dressing" covers dressings such as patches, plasters, bandages and gauze etc. for use in connection with transdermal delivery of agents. The term also includes material in amorphous or liquid form. The term covers dressings for application to body surfaces generally, including internal and external tissues, particularly the skin including the scalp. The present disclosure is based on the beneficial properties of nitric oxide (NO).

The present disclosure relates to a skin dressing comprising a first component including a source of protons, a second component including a nitrite salt, the skin dressing further comprising a non-thiol reductant, such that, when the first and second components are brought together and applied to a skin site, the nitrite reacts to generate nitric oxide, increasing the pH of the dressing in contact with the skin site from an acidic value to a more neutral value.

Nitrite is a compound with $pK_a$ of about 3.4 (at 25° C.). Thus, the nitrite can act as a buffer in the system, capable of maintaining pH in the range between about 3 to about 4. The nitrite generally is an inorganic nitrite salt (or a combination of inorganic nitrite salts) such as sodium nitrite, potassium nitrite, calcium nitrite, magnesium nitrite, and manganese nitrite.

After bringing the two components together (e.g. contacting the two components) and applying to a skin site (e.g. a wound site), the nitrite enters an acidic environment and nitric oxide generation will start. Importantly, an acidic pH will be maintained by the nitrite itself. As the nitric oxide generation proceeds and nitrite concentration decreases, the buffering capacity in the system will decrease. Simultaneously, protons are consumed during nitrite conversion to nitric oxide. Consequently, the pH of the activated system will increase closer to neutral values as the nitrite conversion proceeds toward completion. The system thus exhibits a self-regulation of pH, ensuring milder pH of the topical application once sufficient build-up of nitric oxide is achieved.

Such self-regulation can occur relatively rapidly or more gradually depending on the concentrations of actives in the two components of the system. Importantly, the rate of such self-regulation will be proportional to the rate of nitrite conversion to nitric oxide.

The dressing, typically in use on skin, thus functions as a nitric oxide donor. Nitric oxide is being released on or in the vicinity of the skin being treated. This can be achieved whilst avoiding prolonged exposure of the body site (skin, wound etc.) to an acidic, strongly buffered, dressing application.

If a quick burst of nitric oxide is required then the pH of the composition immediately after activation will be relatively low, possibly around 3.5, but, because of the low pH, nitrite is quickly converted to nitric oxide, resulting in a rapid increase in pH. If a more gradual conversion of nitrite is required then the pH of the composition immediately after activation will not need to be too acidic (possibly between 4 to 4.5, between 4 to 5, and/or between 4.5 to 5), and the shift toward more neutral pH values will be more gradual.

For example, if rapid generation of nitric oxide is required in order to achieve a localised vasodilatation and consequent increase of blood flow then the pH of the formulation immediately after activation must be such that nitrite is efficiently converted to nitric oxide. As this reaction proceeds quickly, the pH rises closer to neutral values. Whilst such increase of pH would slow down or stop the nitrite conversion to nitric oxide, such reaction is no longer needed because most nitrite has already been converted. The dressing thus exerts a self-regulating function.

Therefore, as the nitrite reacts to form nitric oxide the pH of the dressing increases. The pH of the dressing may therefore increase from an acidic value (e.g. below 5, below 4, and/or from 3 to 4) to a more neutral value (e.g. above 5, above 6, and/or from 6 to 7) as the nitrite reacts. For example, the pH will increase from below 4 to above 6.

It may be desirable that the nitrite is the only component which has a $pK_a$ of less than 5 (e.g., less than 4.5, less than 4, from 1 to 4, from 1 to 4.5, and/or from 1 to 5). Therefore, the dressing may be free of any additional materials having a $pK_a$ of less than 5, less than 4.5, less than 4, from 1 to 4, from 1 to 4.5, and/or from 1 to 5.

Typically, the first component is acidic, for example, having a pH in the range of from 2 to 5, from 2 to 3.5, from 3 to 5, and/or from 3 to 4. The second component may have a pH in the range of from 5 to 12, e.g. 6 to 11 and/or from 7 to 10. A small amount of buffer with a $pK_a$ e.g. in the range of from 7 to 12 is optionally present in the second component e.g. at a concentration of from 0.01% to 0.2%, based on the dressing, to maintain the pH.

Appropriate amounts of nitrite, reducing agent and source of protons buffer to achieve the required rate of nitric oxide production and the required pH profile can be readily determined by experiment.

The source of protons can originate from a relatively small concentration of a strong acid providing a pH in the first component of from 2.0 to 3.5. For example, hydrochloric acid can be incorporated in the first component used at concentrations between 0.5 mM to 10 mM.

One disadvantage of using a strong acid as the source of protons is the relatively low pH of the component in which such strong acid is contained (for example, pH about 2 if 10 mM hydrochloric acid is used). Although the pH of the composition will increase to more neutral values following activation, due to the buffering capacity of nitrite, the very low pH of one of the components prior to activation might still be a potential problem for some applications.

Therefore, the source of protons may comprise a weak acid and/or a buffer with a $pK_a$ of from 4.5 to 7.0, e.g. from 5 to 6, and/or about 5.5. Such a buffer may be incorporated in the first component of the dressing. Suitable weak acids and/or buffers may include one or more of sorbic acid ($pK_a$ 4.8), acetic acid ($pK_a$ 4.8), alginic acid ($pK_a$ 5.0), and bicarbonic acid ($pK_a$ 6.3). Additionally, ascorbic acid (pKa 4.1) may be suitable in some embodiments. As discussed above, the first component may be acidic with, for example, a pH of from 2 to 5. At this pH, a very high proportion of the buffer will be present in protonated form and can thus serve as a useful source (or reservoir) of protons. Hence, the pH of the first component may be lower than the $pK_a$ of the source of protons and/or the buffer.

Since the buffering capacity of this buffer is minimal at pH between about 3 to 4, nitrite will be a dominant buffer in the composition following activation. As the conversion of nitrite to nitric oxide proceeds, accompanied by consumption of protons, the buffering capacity of nitrite will diminish and pH will increase. The buffering contribution of the source of protons buffer (with e.g. $pK_a$ about 5.5) will be minimal in the initial stages, but it will prevent the pH from rising too sharply above 4.5, where the conversion of nitrite to nitric oxide is rather inefficient. The pH will only reach those levels if most nitrite is converted, at which point low pH is no longer required as the build-up of nitric oxide has been achieved.

Thus, there is a co-operation between nitrite ($pK_a$ 3.4) and the source of protons buffer ($pK_a$, e.g. about 5.5) in terms of proton exchange, ensuring an efficient conversion of nitrite whilst maintaining a mild pH environment.

The source of protons buffer can be added to the formulation in the form of an additive. Conveniently, it can be incorporated as part of a polymeric support. Preferred polymeric supports comprise polymers based on polyacrylic acid and contain dissociable groups with $pK_a$ between 5 to 6.

As a further possibility, protons may be generated in the dressing on activation, e.g. from an oxidase enzyme/substrate system. An oxidase enzyme catalyses reaction of an appropriate substrate with oxygen to produce hydrogen peroxide and an acid, which dissociates to produce protons. The preferred oxidase/substrate system is glucose oxidase and glucose. Glucose oxidase catalyses oxidation of glucose by oxygen to produce hydrogen peroxide and gluconic acid. Gluconic acid dissociates to produce gluconate anion and a proton and can thus serve as the source of protons:

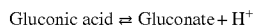

$$\text{Glucose} + O_2 \xrightarrow{\text{Glucose oxidase}} \text{Gluconic acid} + H_2O_2$$

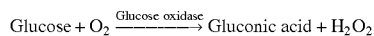

$$\text{Gluconic acid} \rightleftharpoons \text{Gluconate} + H^+$$

The enzyme and corresponding substrate are conveniently incorporated in separate dressing components (which may correspond to or be different from the first and second components discussed above) so they are not in contact prior to activation of the dressing. However, on activation of the dressing, the enzyme and substrate are brought into communication permitting contact, resulting in generation of protons.

Non-thiol reducing agents that are not acids with a $pK_a$ of less than about 5, less than about 4.5, less than about 4, between about 1 to about 4, between about 1 to about 4.5, and/or between about 1 to about 5 may be used as the reductant in the skin dressing. The reductant may be present in the first component, the second component and/or in a third component. Examples of suitable reducing agents include iodide anion, butylated hydroquinone, tocopherol, butylated hydroxyanisole, butylated hydroxytoluene and beta-carotene. For example, non-thiol reducing agents may include one or more of butylated hydroquinone, butylated hydroxyanisole, and butylated hydroxytoluene.

The reductant is typically present in concentrations 0.1% to 5% (w/w) based on the dressing.

Each dressing component conveniently comprises a carrier or support, either in the form of a monomeric matrix or in the form of a polymeric matrix. Each dressing component can be in the form of liquid, amorphous gel or in the form of a layer, e.g. in the form of a sheet, slab or dry film.

As discussed above, particularly convenient support is a polymer based on polyacrylic acid which contains dissociable groups with $pK_a$ between 5 to 6.

The carrier or support conveniently comprises a hydrated hydrogel. A hydrated hydrogel means one or more water-based or aqueous gels, in hydrated form. A hydrated hydrogel can also act to absorb water and other materials exuded from a wound site, enabling the dressing to perform a valuable and useful function by removing such materials from a wound site. The hydrated hydrogel also provides a source of moisture, that can act in use to maintain a wound site moist, aiding healing.

Suitable hydrated hydrogels are disclosed in WO 03/090800. The hydrated hydrogel conveniently comprises hydrophilic polymer material. Suitable hydrophilic polymer materials include polyacrylates and methacrylates, e.g. as supplied by First Water Ltd in the form of proprietary hydrogels, including poly 2-acrylamido-2-methylpropane sulphonic acid (poly-AMPS) and/or salts thereof (e.g. as described in WO 01/96422), polysaccharides e.g. polysaccharide gums particularly xanthan gum (e.g. available under the Trade Mark Keltrol), various sugars, polycarboxylic acids (e.g. available under the Trade Mark Gantrez AN-169 BF from ISP Europe), poly(methyl vinyl ether co-maleic anhydride) (e.g. available under the Trade Mark Gantrez AN 139, having a molecular weight in the range 20,000 to 40,000), polyvinyl pyrrolidone (e.g. in the form of commercially available grades known as PVP K-30 and PVP K-90), polyethylene oxide (e.g. available under the Trade Mark Polyox WSR-301), polyvinyl alcohol (e.g. available under the Trade Mark Elvanol), cross-linked polyacrylic polymer (e.g. available under the Trade Mark Carbopol EZ-1), celluloses and modified celluloses including hydroxypropyl cellulose (e.g. available under the Trade Mark Klucel EEF), sodium carboxymethyl cellulose (e.g. available under the Trade Mark Cellulose Gum 7LF) and hydroxyethyl cellulose (e.g. available under the Trade Mark Natrosol 250 LR).

Mixtures of hydrophilic polymer materials may be used in a gel.

In a hydrated hydrogel of hydrophilic polymer material, the hydrophilic polymer material is desirably present at a concentration of at least 1%, preferably at least 2%, more preferably at least 5%, yet more preferably at least 10%, or at least 20%, desirably at least 25% and even more desirably at least 30% by weight based on the total weight of the gel. Even higher amounts, up to about 40% by weight based on the total weight of the gel, may be used.

Good results have been obtained with use of a hydrated hydrogel of poly-AMPS and/or salts thereof in an amount of about 30% by weight of the total weight of the gel.

By using a gel comprising a relatively high concentration (at least 2% by weight) of hydrophilic polymer material, the gel can function particularly effectively to take up water in use of the dressing, e.g. from serum exudates while in contact with a wound. Because the gel is an aqueous system, use of the dressing does not have the effect of inducing an overall dryness of the wound which would be undesirable. This is because water vapour pressure is maintained in the enclosed environment surrounding the skin in use of the dressing. The gel thus functions as an absorbent entity for the removal of moisture, e.g. wound exudate, that also provides a helpful background level of excess moisture.

The water-uptake capacity of a hydrated hydrogel, including a high concentration gel, enables the dressing to aid wound healing by removing substantial amounts of exudates, swelling-up as it does so. By using a carefully formulated, ready-hydrated gel, the wound is prevented from reaching a state of unhelpful dryness. Ready hydration also ensures the quick formation of an aqueous liquid interface between the dressing and the wound, thus preventing adhesion, which otherwise would interfere with easy lifting of the dressing when it has to be replaced. A good aqueous liquid interface between the wound and the dressing is also important in allowing any beneficial products carried in the gel to enter the wound through all of the available surface.

The hydrated hydrogel material is typically in the form of a solid layer, sheet or film of material that is typically cross-linked, and that may incorporate a mechanical reinforcing structure. The size and shape of the layer, sheet or film can be selected to suit the intended use of the dressing. Thicknesses in the range 0.05 to 5 mm, preferably 0.5 to 3 mm are particularly suitable.

Alternatively, the hydrated hydrogel may be in the form of an amorphous gel, not having a fixed form or shape, that can be deformed and shaped in three dimensions, including being squeezed through a nozzle. Amorphous gels are typically not cross-linked or have low levels of cross-linking. A shear-thinning (thixotropic) amorphous gel may be used. Such a gel is liquid when subjected to shear stress (e.g. when being poured or squeezed through a nozzle) but set when static. Thus the gel may be in the form of a pourable or squeezable component that may be dispensed, e.g. from a compressible tube or a syringe-like dispenser, comprising a piston and cylinder, typically with a nozzle of about 3 mm diameter. Amorphous gels allow efficient mixing of the two-component system. Such a gel may be applied in the form of a surface layer, or into a wound cavity as a fully conformable gel that fills the available space and contacts the wound surface.

A typical example of an amorphous gel formulation is: 15% w/w AMPS (sodium salt), 0.19% polyethylene glycol diacrylate and 0.01% hydroxycyclohexyl phenyl ketone, with the volume made up to 100% with analytical grade DI water. The reagents are thoroughly mixed and dissolved, then polymerised for between 30-60 seconds, using a UV-A lamp delivering approximately 100 mW/cm$^2$, to form the required hydrogel. This may be contained in plastic syringes from which the amorphous gel may then be dispensed from a syringe to a target site, as a surface layer or to fill a cavity.

In one embodiment, the dressing comprises two components which are amorphous. The components can be in the form of e.g. a gel, semi-solid, cream, paste, emulsion, lotion, thickened solution, or liquid e.g. an aqueous solution. Amorphous components may be thixotropic, exhibiting shear thinning. Hydrated hydrogels may be conveniently employed, as discussed above.

The two amorphous components are kept separate until it is desired to apply the dressing to a body surface. Conveniently, they are packaged in a container having a nozzle, through which the amorphous components can be delivered. The two components may be packaged in a two compartment dispenser, preferably being operable to deliver both components simultaneously. For example, the two components may be contained in separate compartments of a squeezable package (e.g. tube) that is configured to be manipulated to mix (e.g. knead) the components together in the package and then dispense the mixed components from the package.

The dressing optionally includes, or is used with, a covering or outer layer for adhering the dressing to the skin of a human or animal in a known manner.

Dressings in accordance with the present disclosure can be manufactured in a range of different sizes and shapes to enable efficient application onto an area of the body.

Dressing components are suitably stored prior to use in sterile, sealed, water-impervious packages, e.g. dual-chamber plastic tubes or laminated aluminium foil packages.

In use, the dressing component or components are removed from their packaging and e.g. are mixed appropriately on the skin of a human or animal, e.g. over a region of skin to be treated for cosmetic or therapeutic purposes. The dressing may be activated prior to or during application onto skin. The dressing may also be used as an adjuvant for transdermal delivery.

EXAMPLES

Skin dressings, and related compositions and methods, may be further understood with reference to the following illustrative, non-exclusive examples.
Materials and Methods
  Chemicals & Other Materials
  Water (conductivity<10 μS cm$^{-1}$; either analytical reagent grade, Fisher or Sanyo Fistreem MultiPure)
  Sodium nitrite, from Sigma (S2252)
  Thioglycerol, from Fluka (88641)
  Hydroquinone, from Sigma (H9003)
  Hydrochloric acid, from Fisher (J/4310/17)
Measurement of S-Nitrosothiol Concentration in Aqueous Solutions
  The following reagents were prepared:
  Reagent 1: Na-phosphate buffer (pH 7.4, 0.1 M)
  Reagent 2: Griess reagent: 20 mg of N-(1-Naphthyl)ethylendiamine dihydrochloride (HADD)+500 mg of sulphanilamide dissolved in 2 mL of DMSO. (N. B. This solution is light sensitive and should be kept in the dark as much as possible.)
  Reagent 3: Mercuric chloride (10 mM) in DMSO (13.58 mg of HgCl$_2$ in 5 mL of DMSO)
  The six-step procedure set out below was then followed:
  Dispense 1.5 mL of Reagent 1 into a plastic cuvette Add 200 μL of the sample (i.e. sample in which GSNO concentration is to be determined)

Add 1.17 mL of DI water

Add 100 μL of Reagent 2

Add 30 μL of Reagent 3 and give the solution a good mix

Read absorbance of the resulting mixture at 496 nm in 10 min.

Figure 2:
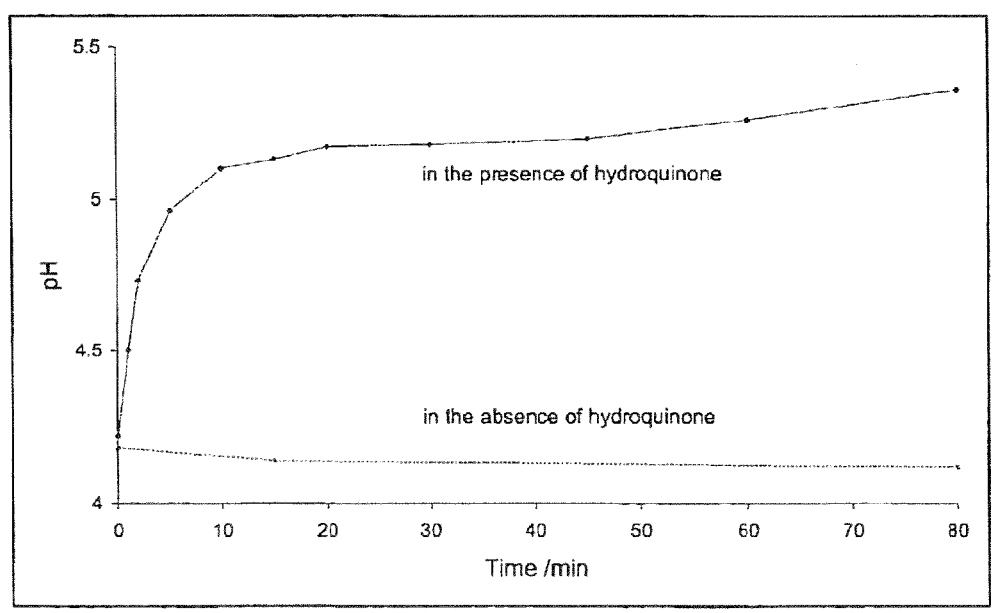
FIG. 2 is a graph of pH versus time (in minutes) showing the effect of hydroquinone (30 mM) on the pH of acidified nitrite (30 mM). Nitrite was acidified by addition of hydrochloric acid (final concentration 4 mM). The pH was measured prior to addition of hydroquinone and then at time-points indicated following addition of hydroquinone.

The concentration of nitrosothiol concentration can be estimated from the absorbance reading using the molar absorption coefficient for nitrosothiols=approximately 10,000 $M^{-1}$ $cm^{-1}$. Example 1: Changes of pH resulting from generation of nitric oxide in a mixture containing hydroquinone and an unbuffered acidified solution of sodium nitrite pH was measured in a solution of acidified nitrite both in the absence and in the presence of hydroquinone (i.e. an example of a non-thiol reducing compound). Nitrite was acidified by addition of hydrochloric acid to achieve a final concentration of 10 mM (FIG. 1) or 4 mM (FIG. 2). If 10 mM hydrochloric acid was used to acidify the reaction mixture pH was maintained at approximately 3.8 in the absence of the reducing agent. In contrast, the presence of hydroquinone resulted in a rapid increase of pH to about 5.0 followed by a further slow increase. A similar pH profile was observed if 4 mM hydrochloric acid was used to acidify the mixture (FIG. 2), except that in this case the initial pH was higher (about 4.2). In both cases the increase of pH was accompanied by formation of gas bubbles in the mixtures, reflecting the formation of nitric oxide in the mixtures. No bubble formation was observed in the absence of the reducing agent.

The example demonstrates the ability of the nitric oxide generating system to regulate its pH in the absence of buffers with $pK_a$ between about 1 to about 4. The actual rate of the nitric oxide generation can be regulated by the degree of acidification of the system.

The invention claimed is:

1. A skin dressing comprising:
   a first component including a source of protons comprising at least one weak acid selected from the group consisting of sorbic acid, acetic acid, and bicarbonic acid;
   a second component including a nitrite salt; and
   a non-thiol reductant selected from the group consisting of butylated hydroquinone, butylated hydroxyanisole, and butylated hydroxytoluene;
   wherein the skin dressing is adapted such that, when the first and second components are brought together and applied to a skin site, the nitrite reacts to generate nitric oxide, increasing a pH of the skin dressing in contact with the skin site from an acidic value to a more neutral value; and
   wherein the source of protons includes a buffer with a $pK_a$ of from 4.5 to 7.0.

2. The skin dressing of claim 1, wherein the nitrite is the only component having a $pK_a$ of less than 4.5.

3. The skin dressing of claim 1, wherein the nitrite is the only component having a $pK_a$ of from 1 to 4.

4. The skin dressing of claim 1, wherein a pH of the first component is from 2 to 5.

5. The skin dressing of claim 1, wherein, as the nitrite reacts to generate nitric oxide or a nitric oxide donor, the pH of the skin dressing in contact with the skin increases from below 5 to above 5.

6. The skin dressing of claim 1, wherein a pH of the second component is from 5 to 12.

7. The skin dressing of claim 1, wherein the first and the second components are amorphous.

8. The skin dressing of claim 1, wherein the first component and/or the second component comprise a polymeric support.

9. The skin dressing of claim 8, wherein the first component comprises a polymeric support based on polyacrylic acid.

10. A skin dressing comprising:
    a first component including:
    a) a non-thiol reductant selected from the group consisting of butylated hydroquinone, butylated hydroxyanisole, and butylated hydroxytoluene,
    b) at least one weak acid selected from the group consisting of sorbic acid, acetic acid, and bicarbonic acid, and
    c) a buffer with a $pK_a$ of from 4.5 to 7.0; and
    a second component including a nitrite salt;
    wherein the skin dressing is adapted, when the first component and the second component are brought together and applied to a skin site, to generate nitric oxide by reacting the nitrite, and to increase a pH of the skin dressing in contact with the skin site from an acidic value to a more neutral value.

11. The skin dressing of claim 10, wherein the nitrite is the only component having a $pK_a$ of from 1 to 4.

12. The skin dressing of claim 10, wherein a pH of the first component is from 2 to 5.

13. The skin dressing of claim 10, wherein a pH of the second component is from 5 to 12.

14. The skin dressing of claim 10, wherein the first and the second components are amorphous.

15. The skin dressing of claim 14, wherein the first component comprises a polymeric support and the second component comprises a polymeric support.

* * * * *